US007266411B1

(12) United States Patent
Paris et al.

(10) Patent No.: US 7,266,411 B1
(45) Date of Patent: Sep. 4, 2007

(54) IMPLANTABLE CARDIAC STIMULATION DEVICE AND METHOD PROVIDING DYNAMIC SENSING CONFIGURATIONS FOR BICHAMBER STIMULATION AND TACHYARRHYTHMIA DETECTION

(75) Inventors: Michael Paris, San Francisco, CA (US); Eric Husky, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 273 days.

(21) Appl. No.: 11/120,459

(22) Filed: May 2, 2005

(51) Int. Cl.
*A61N 1/365* (2006.01)
(52) U.S. Cl. .................. 607/18; 607/9; 607/15
(58) Field of Classification Search .............. 607/18
See application file for complete search history.

(56) References Cited

U.S. PATENT DOCUMENTS

| 5,865,838 | A | 2/1999 | Obel et al. .................. 607/5 |
|---|---|---|---|
| 6,473,645 | B1 | 10/2002 | Levine ........................ 607/9 |
| 6,477,417 | B1 | 11/2002 | Levine ........................ 607/9 |
| 6,477,420 | B1 | 11/2002 | Struble et al. ............... 607/14 |
| 6,606,516 | B2 | 8/2003 | Levine ........................ 607/9 |
| 6,611,714 | B1 | 8/2003 | Mo ........................... 607/27 |
| 6,654,639 | B1 | 11/2003 | Lu ............................ 607/17 |
| 2002/0082660 | A1* | 6/2002 | Stahmann et al. ........... 607/14 |
| 2003/0069610 | A1* | 4/2003 | Kramer et al. .............. 607/25 |

\* cited by examiner

*Primary Examiner*—Carl Layno
*Assistant Examiner*—Yun Haeng Lee
(74) *Attorney, Agent, or Firm*—Steven M. Mitchell

(57) ABSTRACT

An implantable cardiac stimulation device provides bichamber pacing and dynamic bichamber and single chamber sensing. The device includes a sensing circuit that senses activity of a heart, a lead system coupled to a plurality of chambers of the heart, and a cardiac rate circuit that determines a cardiac rate of the heart. A control circuit causes the lead system to couple the sensing circuit to corresponding chambers of the heart to enable bichamber trigger pacing when the cardiac rate is below a given rate and to a single chamber of the heart when the cardiac rate is above the given rate to enable enhanced tachycardia sensing.

13 Claims, 3 Drawing Sheets

IMPLANTABLE CARDIAC STIMULATION DEVICE AND METHOD PROVIDING DYNAMIC SENSING CONFIGURATIONS FOR BICHAMBER STIMULATION AND TACHYARRHYTHMIA DETECTION

FIELD OF THE INVENTION

The present invention generally relates to an implantable cardiac stimulation device that provides electrical therapy to a patient's heart. The present invention more particularly relates to such a device that provides bichamber pacing and tachyarrhythmia detection with selectable sensing electrode configurations.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered to be comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied or intrinsic responses are sensed between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied or intrinsic responses are sensed between a pair of closely spaced electrodes carried by the lead, in electrical contact with the desired heart chamber, with the most proximal electrode serving as the anode and the most distal electrode serving as the cathode.

Pacemakers deliver pacing pulses to the heart to induce a depolarization and a mechanical contraction of that chamber when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Recently, there has been the introduction of pacing systems that stimulate in corresponding chambers of the heart as, for example, the right ventricle (RV) and left ventricle (LV). These are termed biventricular stimulation devices. Biventricular pacing has been shown to coordinate contractions of the left and right ventricles, reduce the amount of blood flow that leaks through the mitral valve, and decreases the motion of the septal wall that separates the chambers of the heart. Such motion can affect the quantity of blood that the ventricle can pump out in a single beat.

Biventricular pacing has been found to be particularly advantageous in patients suffering from congestive heart disease because of the improved ability of the left ventricle to fully pump blood from the heart. As a result, patients are able to tolerate greater exertion, have a longer life span, and experience a higher quality of life.

Biatrial pacing has also been suggested to also lend in coordinating contractions of the right and left atria. As used herein, the term corresponding chambers is meant to refer to either the combination of the right and left atria or the combination of the right and left ventricles.

One form of biventricular pacing is referred to as Cardiac Resynchronization Therapy (CRT). It has been shown to have a particular positive effect on patients with heart failure (HF). There are a number of ways CRT may be performed. For example, during an atrial tracking mode (DDD), the AV/PV intervals may be set to be short, a negative hysteresis value can be used to ensure pacing, or a trigger mode may be established to provide a pacing stimulation pulse upon a sensed event. For non-tracking modes (DDI, VVI) a high ventricular pacing rate or triggered pacing may be used.

Triggered pacing offers the patient a more physiologic AV/PV delay (as it is their own intrinsic rate) and ensures high percentage of pacing during times of atrial tachycardia (AT) or atrial fibrillation (AF), a critical time for HF patients to receive CRT therapy. However, for triggered pacing to be truly effective in synchronization, the sensing should come from the left and right ventricles. Additionally, sensing from both of these corresponding chambers will ensure that long conduction delays or premature ventricular contractions (PVCs) do not cause extra harm from pacing into a vulnerable period that may come from sensing from one chamber only. For example, a PVC may occur on the left side and be sensed over 100 ms later in the right side to which the device would elicit a biventricular pace pulse into a potential vulnerable period.

Using a combined sensing configuration (left and right ventricle) however poses a problem with accurate ventricular tachycardia and fibrillation detection. For example, if the patient has a very wide QRS complex (which is very likely with an HF patient), then combined right and left sensing may cause the device to double count, thus delivering a more aggressive therapy than may be necessary, i.e., fibrillation therapy instead of antitachycardia pacing (ATP) therapy, or even an inappropriate therapy.

For devices with independent right and left sensing, this may not pose such a problem. But for devices that have limited sense channels, an approach that could encompass right and left sensing while pacing and right sensing while in a tachycardia would be preferred. The present invention addresses this and other issues.

SUMMARY OF THE INVENTION

The invention provides an implantable cardiac stimulation device comprising a sensing circuit that senses activity of a heart, a lead system coupled to a plurality of chambers of the heart, and a cardiac rate circuit that determines a cardiac rate of the heart. The device further comprises a control circuit that causes the lead system to couple the sensing circuit to corresponding chambers of the heart when the cardiac rate is below a given rate and to a single chamber of the heart when the cardiac rate is above the given rate.

The device may further comprise a pulse generator that provides pacing pulses to the corresponding chambers of the heart. The pulse generator may provide simultaneous pacing pulses or sequential pacing pulses to the corresponding chambers of the heart. The pulse generator may provide the pacing pulses in a trigger mode up to a given rate limit which may be a maximum trigger rate.

The corresponding chambers may be the right ventricle and the left ventricle of the heart. The single chamber may be one of the ventricles of the heart. More particularly, the single chamber may be the right ventricle.

The corresponding chambers may alternatively be the right atrium and the left atrium of the heart. The single chamber may then be one of the atria of the heart. More particularly, the single chamber may be the right atrium.

The cardiac rate circuit may determine the cardiac rate for each heartbeat and the control circuit may cause the lead system to transition from coupling the sensing circuit to the single chamber to coupling the sensing circuit to the corresponding chambers of the heart after the rate has been below the given rate for a predetermined number of heartbeats.

The invention further provides an implantable cardiac stimulation device comprising a sensing circuit that senses cardiac activity of a heart, a lead system coupled to a plurality of chambers of the heart, and a pulse generator that provides pacing pulses to corresponding chambers of the heart responsive to the sensing circuit. The device further comprises a cardiac rate circuit that determines a cardiac rate of the heart, and a control circuit that causes the lead system to couple the sensing circuit to the corresponding chambers of the heart when the rate is below a maximum rate and to only one of the corresponding chambers when the rate is above the maximum rate.

The invention still further provides a method for use in an implantable cardiac stimulation device. The method comprises determining a cardiac rate associated with interaction of the device and the heart and sensing cardiac activity of the heart. The sensing step includes a first sensing step of sensing cardiac activity of corresponding chambers of the heart when the cardiac rate is below a given rate and a second sensing step of sensing cardiac activity of a single chamber of the heart when the cardiac rate is above the given rate.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
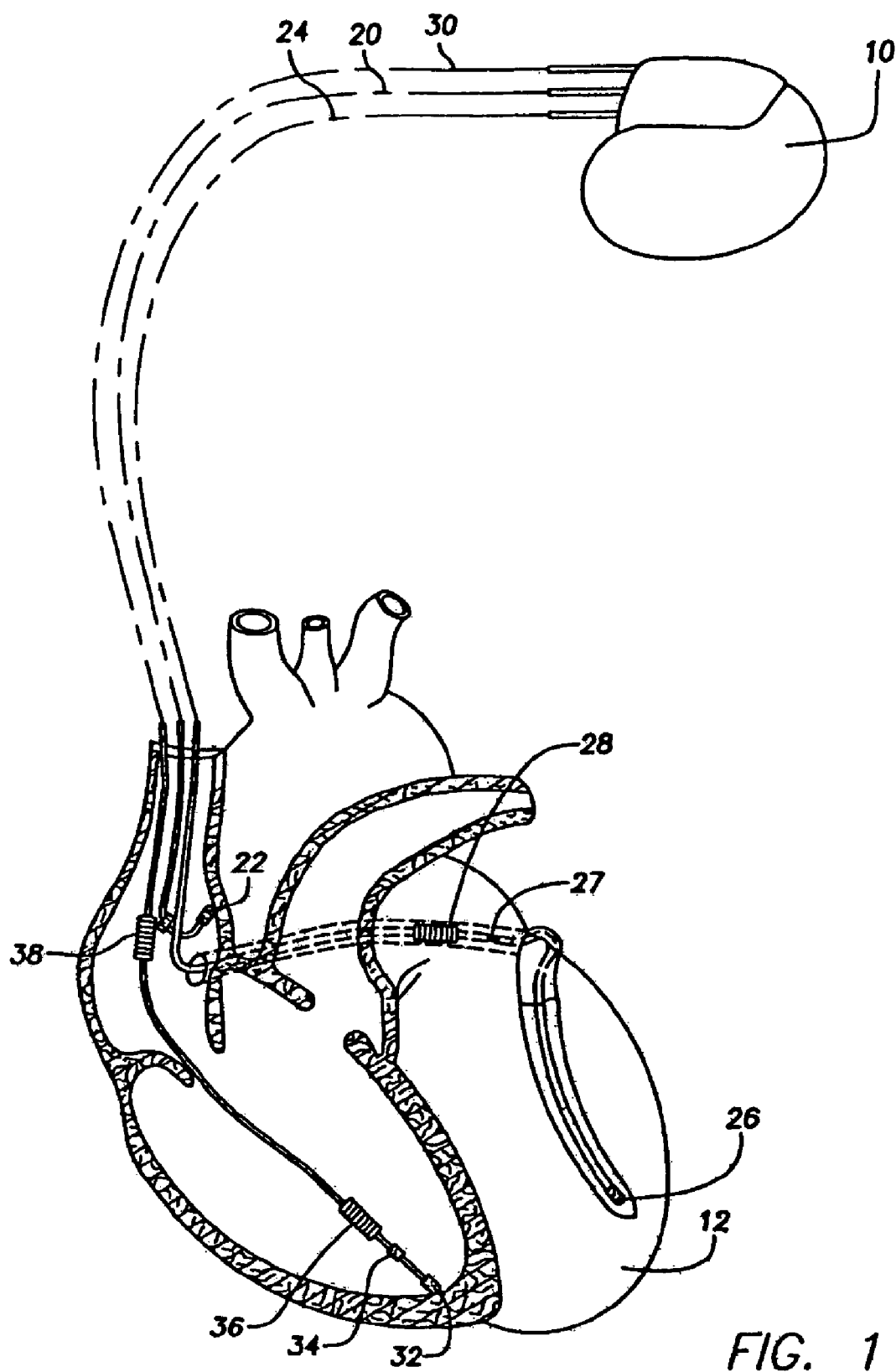
FIG. 1 is a simplified diagram illustrating an implantable stimulation device according to an embodiment of the invention in electrical communication with a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
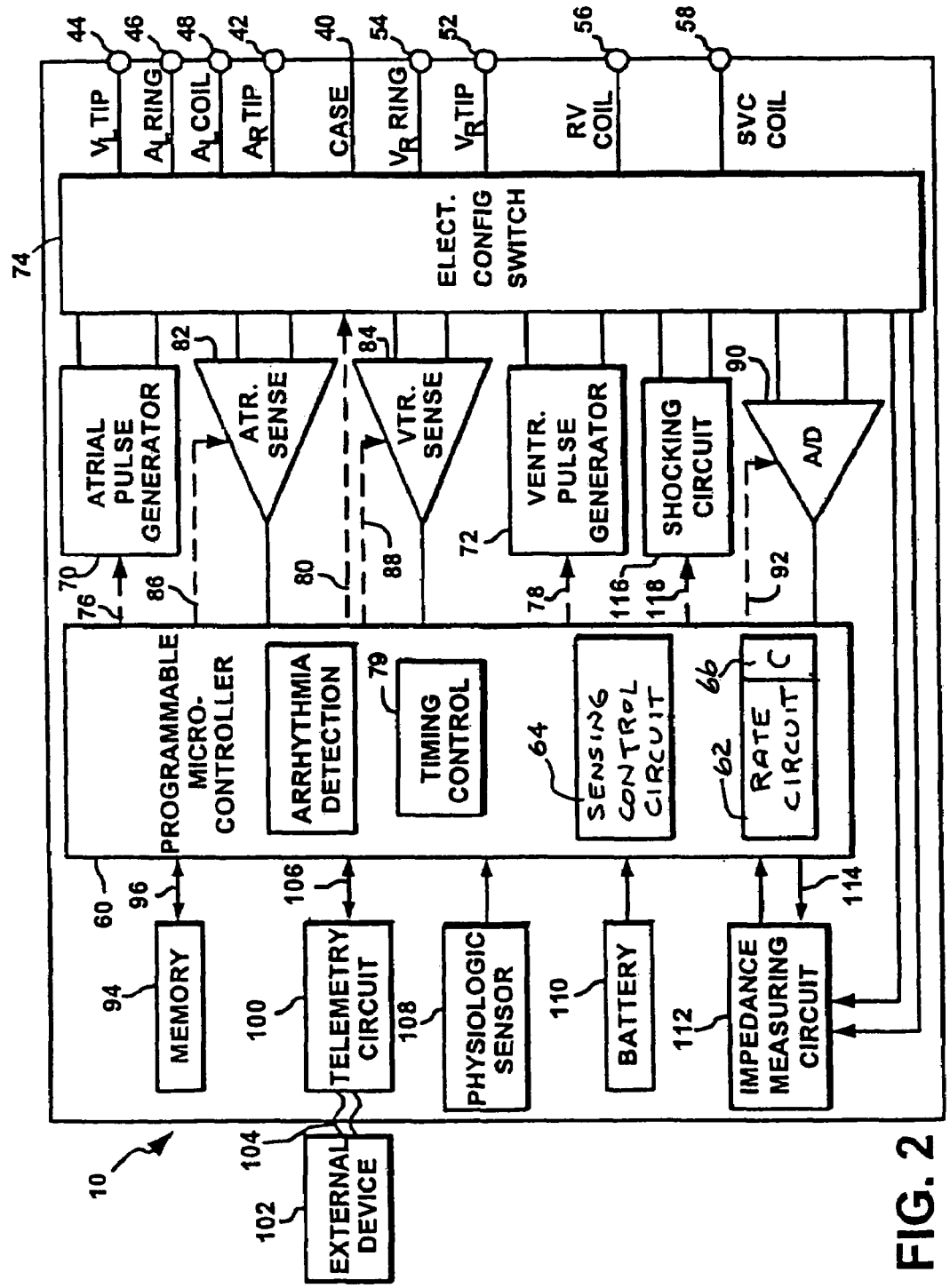
FIG. 2 is a functional block diagram of the implantable stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as are known in the art.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As may be further noticed with reference to FIG. 2, the device 10 further includes a rate circuit 62 and a sensing control circuit 64. The device 10 may be programmed to provide pacing pulses in any one of a plurality of pacing modes including single chamber, bichamber coupled or bichamber sequential pacing modes. Any one of the electrodes previously described may be employed for this purpose as may the case electrode 40. Preferably, in accordance with this embodiment, the device is programmed to provide biventricular pacing with the ventricular pulse generator 72 being coupled to both electrode 32 and electrode 26. Using the case 40 as a return electrode, pacing pulses may be applied to these electrodes and hence the right and left ventricles. The pacing pulses may be provided simultaneously (biventricular coupled) or sequentially. In this embodiment, the pacing pulses are provided in a trigger mode wherein an intrinsic activation of either chamber results in the immediate application of the simultaneous pacing pulses to both chambers. Further, the ventricular sense amplifier 84 is likewise coupled to these electrodes for sensing the intrinsic activations, and blanked during delivery of the pacing pulses.

The above configuration and operating mode maintained as long as the pacing rate remains below the maximum triggering rate (MGR). If the rate circuit 62 determines a sensing rate exceeding the MGR, a ventricular tachycardia may be present. To avoid the possible double counting of ventricular events by the arrhythmia detector, in accordance with this embodiment, the sensing control circuit 64 causes the switch 74 to couple the ventricular sense amplifier 84 to only the right ventricle with, for example, electrode 32 for sensing only in the right ventricle of the heart. This sensing configuration is maintained until the rate circuit 62 determines that the sense rate has been below the MGR for at least a given number (Y) of heartbeats. This ensures that the tachycardia has ended and that it is safe to transition back to biventricular sensing.

In accordance with this embodiment, the given number (Y) may be a consecutive number or Y heartbeats out of the last Z heartbeats. Further, in accordance with this embodiment, Y may be ten (10) and the MTR may be 130 bpm, for example. For counting the Y heartbeats, the rate circuit 62 includes a counter 66.

Figure 3:
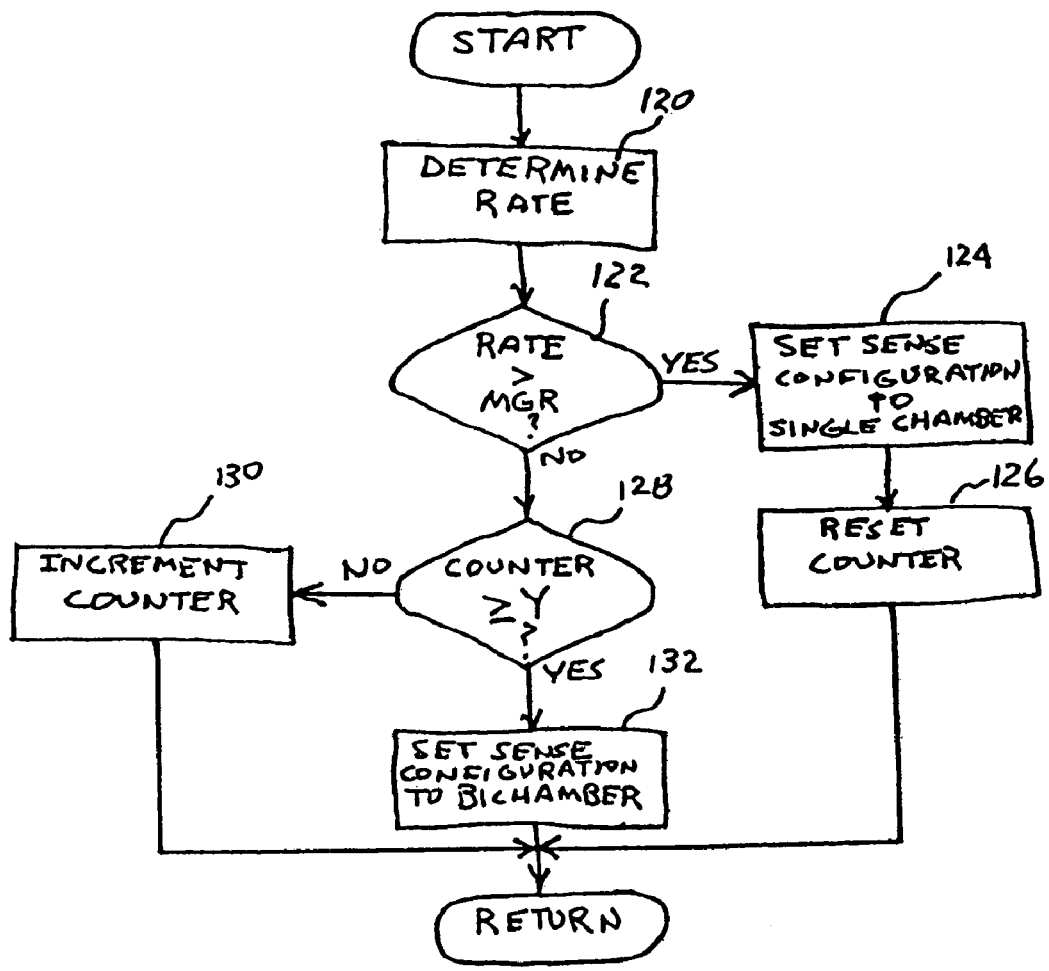
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow chart presented herein provides the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 is initiated and completes on a beat-by-beat basis. It initiates with activity block 120 wherein the rate circuit 62 determines the current sense (trigger) rate. The process then advances to decision block 122 wherein the rate circuit determines if the current sense (trigger) rate is above the MGR. If it is, evidencing a potential tachyarrhythmia, the process advances to activity block 124 wherein the control circuit 64 causes the switch 74 to set the sensing configuration for sensing only in the right ventricle. The process then advances to activity block 126 to reset counter 66 before returning.

If in decision block 122 it is determined by the rate circuit 62 that the current sense (trigger) rate is below the MGR, the process advances to decision block 128. In decision block 128, the rate circuit determines if the count in counter 66 is equal to or greater than the given number (Y). If it is not, indicating that the device has been sensing only in the right ventricle and that the trigger rate has not been below the MGR for enough heartbeats to enable a sensing configuration transition, the process advances to activity block 130 to increment counter 66. The process then returns.

If in decision block 128 it is determined that the counter is equal to or greater than the given number (Y), the process advances to activity block 132. Here, the control circuit 62 causes the switch 74 to couple the sense amplifier 84 for sensing activity of both the right and left ventricles if previously, sensing of only right ventricular activity was being performed, or to maintain a prior biventricular sensing configuration. Hence, the transition from single chamber sensing to biventricular sensing has hysteresis to assure that the possible tachyarrhythmia has lapsed before the transition occurs.

While this embodiment has been primarily directed to biventricular pacing and sensing it will be appreciated by those skilled in the art that the foregoing could be applied equally as well to the corresponding chambers of the right and left atria. Biatrial sensing may be performed with electrodes 22 and 27. Single chamber sensing only may be performed with electrode 22.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. In an implantable cardiac stimulation device, a method of sensing activity of a heart comprising:

determining a cardiac rate associated with interaction of the device and the heart; and sensing cardiac activity of the heart, the sensing step including a first sensing step of sensing cardiac activity of corresponding chambers of the heart when the cardiac rate is below a given rate and a second sensing step of sensing cardiac activity of a single chamber of the heart when the cardiac rate is above the given rate.

2. The method of claim 1 including the further step of providing pacing pulses to the corresponding chambers of the heart responsive to sensing cardiac activity of the heart.

3. The method of claim 2 wherein the providing step includes providing simultaneous pacing pulses to the corresponding chambers of the heart.

4. The method of claim 2 wherein the providing step includes providing sequential pacing pulses to the corresponding chambers of the heart.

5. The method of claim 2 wherein the providing step includes providing the pacing pulses in a trigger mode.

6. The method of claim 5 wherein the given rate is below a maximum trigger rate.

7. The method of claim 1 wherein the corresponding chambers are a right ventricle and a left ventricle of the heart.

8. The method of claim 7 wherein the single chamber is one of the ventricles of the heart.

9. The method of claim 8 wherein the single chamber is the right ventricle.

10. The method of claim 1 wherein the corresponding chambers are a right atrium and a left atrium of the heart.

11. The method of claim 10 wherein the single chamber is one of the atria of the heart.

12. The method of claim 11 wherein the single chamber is the right atrium.

13. The method of claim 1 wherein the determining step includes determining the cardiac rate for each heartbeat and wherein the sensing step further includes transitioning from sensing cardiac activity of the single chamber to sensing the cardiac activity of the corresponding chambers of the heart after the rate has been below the given rate for a predetermined number of heartbeats.

* * * * *